US007756727B1

(12) United States Patent
Greenspan et al.

(10) Patent No.: US 7,756,727 B1
(45) Date of Patent: Jul. 13, 2010

(54) METHOD AND APPARATUS FOR CASE BUILDING AND PRESENTATION OF HEALTHCARE PROCEDURES

(75) Inventors: Larry A. Greenspan, Sparks, MD (US); Steven Michael Mallot, Towson, MD (US); Jon David Frizzell, Manchester, MD (US); Deborah Louise Reed, Towson, MD (US); Brian Howard, Baltimore, MD (US)

(73) Assignee: Carestream Health, Inc., Rochester, NY (US)

( * ) Notice: Subject to any disclaimer, the term of this patent is extended or adjusted under 35 U.S.C. 154(b) by 1998 days.

(21) Appl. No.: 09/722,962

(22) Filed: Nov. 27, 2000

Related U.S. Application Data

(60) Provisional application No. 60/234,103, filed on Sep. 21, 2000.

(51) Int. Cl.
*G06F 19/00* (2006.01)
*G06F 17/00* (2006.01)
*G09B 23/28* (2006.01)
(52) U.S. Cl. .......................... 705/3; 715/235; 434/263
(58) Field of Classification Search .................. 705/2, 705/3
See application file for complete search history.

(56) References Cited

U.S. PATENT DOCUMENTS

| 4,945,476 | A | * | 7/1990 | Bodick et al. ............... 600/301 |
| 5,799,282 | A | * | 8/1998 | Rakshit et al. .................. 705/2 |
| 6,014,630 | A | * | 1/2000 | Jeacock et al. .................. 705/3 |
| 6,084,581 | A | * | 7/2000 | Hunt ....................... 715/500.1 |
| 6,171,112 | B1 | * | 1/2001 | Clark et al. .................. 434/322 |
| 6,542,163 | B2 | * | 4/2003 | Gorbet et al. ............... 345/711 |
| 6,587,828 | B1 | * | 7/2003 | Sachdeva ......................... 705/1 |
| 2002/0022973 | A1 | * | 2/2002 | Sun et al. ........................ 705/3 |
| 2002/0062228 | A1 | * | 5/2002 | Portnoy et al. ................. 705/3 |
| 2006/0064329 | A1 | * | 3/2006 | Abolfathi et al. .............. 705/3 |

FOREIGN PATENT DOCUMENTS

WO    WO 9712544 A1 * 4/1997

OTHER PUBLICATIONS

Parker, Roger C., Microsoft 4 for Wiindows for Dummies, 1994, IDG Books Worldwide Inc, pp. 161-200.*
Parker, Roger C., Microsoft Office 4 for Windows for Dummies, 1994, pp. 161-200, published by IDG Books Worldwide, Inc.
Algeo, David, Computers Helping Patients Make Decisions on Treatment, Denver Post, Nov. 3, 1995, Section C01, paragraphs 5-7, 21-26.
Patent Cooperation Treaty, International Search Report, Dec. 27, 2001, International Appl. No. PCT/US01/29533, filed Sep. 20, 2001 by Applicant SoftDent, LLC.

* cited by examiner

*Primary Examiner*—Gerald J. O'Connor
*Assistant Examiner*—R. L Porter

(57) ABSTRACT

A presentation detailing a recommended course of treatment to a patient, frequently referred to as a case, is constructed with a single action. The presentation describes recommended healthcare procedures for a given patient using information specific to that patient's healthcare record. The presentation is constructed by assembling information on the recommended healthcare procedures and all necessary clinical and financial information for the patient stored in a healthcare management desktop application into a template having a format accepted by any standard presentation software program. Finally, using the presentation software program, the recommended course of treatment is presented to the patient. In addition, the presentation software program includes tools to permit customization and storage of each constructed presentation.

29 Claims, 14 Drawing Sheets

| Type | Code | Tooth | Surface | Date | Description |
|---|---|---|---|---|---|
| A | 6752 | 10 | | 08/23/00 | Porcelain Crown Noble Metal (bridge) |
| A | 6010 | 7 | | 08/23/00 | Endosseous Implant |
| A | 5310 | | | 07/28/98 | Teeth And Clasps Extra Per Unit |
| A | 2950 | 6 | | 07/17/00 | Crown Build-up |

Actual Transactions (Right Click on List for View Options)

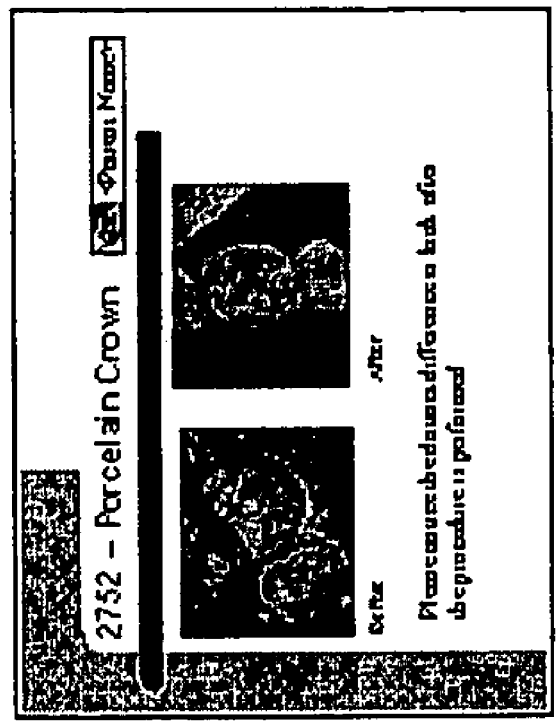
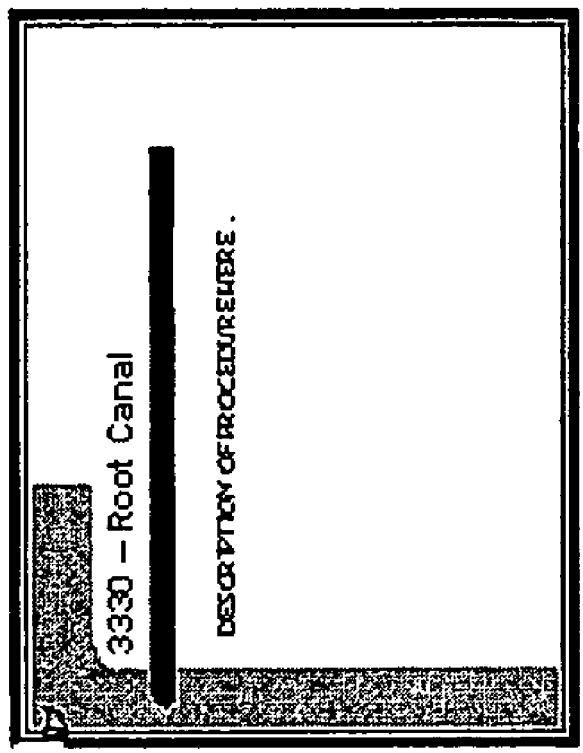
Figure 4

METHOD AND APPARATUS FOR CASE BUILDING AND PRESENTATION OF HEALTHCARE PROCEDURES

CROSS-REFERENCE TO RELATED APPLICATIONS

This application claims the benefit of U.S. Provisional Patent Application No. 60/234,103 filed on Sep. 21, 2000.

BACKGROUND OF THE INVENTION

The present invention is related generally to the field of healthcare management applications. Specifically, the present invention is related to an application that generates a graphical case presentation of a course of treatment using a single mouse click to assemble all necessary information for a diagnosed case from a healthcare management application and consolidate the information into a concise and presentable form for the patient.

Although the tools of the healthcare trade have changed and evolved over the years, the basic practice of medicine or dentistry has always consisted of diagnosing the condition of a patient, charting or documenting the condition, planning the course of treatment, constructing and presenting the treatment plan to the patient, selling or explaining the treatment plan to the patient, and then performing the subsequent work. Healthcare professionals go through rigorous formal education on the medical and clinical aspects above: diagnosing, charting, planning treatment, and performing treatment. However, the construction, presentation, and selling of proposed treatments are not the major focus of a healthcare professional's education.

The billing for healthcare procedures is established as a standard set of codes developed and approved by the governing organizational body. In the case of dentistry, it is the American Dental Association (ADA). Dental billing codes are known as the CDT-3 codes (Current Dental Terminology Revision 3) and are often referred to as the "ADA codes" or procedure codes that define the specific treatments administered and billed for by a dentist. An example ADA code is D3333, which defines the internal root repair of perforation defects procedure. All dentists use this standard nomenclature for defining work planned or performed. Both the ADA and the insurance industry abide by this standard. Similar sets of codes exist in other healthcare arenas.

With the advances in technology over the past 20 years and specifically the development of powerful desktop computers, the practice of healthcare has evolved to take advantage of these new tools and technological advances that improve productivity and generate new revenue opportunities for the healthcare professional. In the case of dentistry, most dental offices today use practice and clinical management software to automate the daily tasks of running a dental office. Although information and functionality vary among the different systems on the market, most track critical information such as guarantors, patients, insurance information, medical history, prescriptions, billing information, recall information, treatment plans and work performed, full restorative dental charts, periodontal charts, digital x-rays, digital camera images and estimated insurance payments. Practice management software has become one of the de facto desktop computer applications for the dental field. The use of practice management software is also prevalent in other healthcare disciplines.

In parallel with the advancement of the "Healthcare Desktop Application", powerful general business software has evolved during the same period. One type of business software tool that has been developed automates the task of organizing and creating presentations. The created presentations are frequently in the form of slide shows. Examples of this type of tool include Microsoft PowerPoint®, StarOffice Impress from Sun Microsystems or any other similar type of presentation tool. These presentation tools afford the user the ability to quickly and easily assemble, organize, generate and show powerful presentations, in video slide or printed formats, to an individual or group. However, even with presentation software tools it is still difficult and time consuming for a healthcare professional to use the presentation software to generate a presentation on proposed courses of treatment for a patient. The healthcare professional must take the time to generate each slide individually, or at a minimum, copy and edit previously used slides. In addition, the transfer of the patient's information into the presentation software is not automatic, leaving many opportunities for errors.

Therefore, what is needed is an application that permits a healthcare professional to generate quickly and easily a presentation of proposed treatments for a patient that includes current and accurate information about the patient.

SUMMARY OF THE INVENTION

A preferred embodiment of the present invention is directed to a process for constructing a presentation detailing a recommended course of treatment to a patient, frequently referred to as a case, with a single action. The presentation is constructed by assembling from a healthcare management desktop application all necessary clinical and financial information for that patient into a format acceptable by any standard presentation software program, e.g. Microsoft PowerPoint. Then, using the presentation software program, the recommended course of treatment is presented to the patient.

Another embodiment of the present invention is directed to a method for generating a presentation describing a recommended course of treatment for an individual. The method includes the step of selecting a presentation template for a presentation. The presentation template is configured for display by a presentation tool. The method also includes the steps of incorporating information on each healthcare procedure included in a recommended course of treatment for an individual into the presentation template to generate an intermediate presentation and incorporating healthcare information specific to the individual from a healthcare desktop application into the intermediate presentation to generate a final presentation. Finally, the method includes the step of storing the final presentation in the healthcare desktop application.

Still another embodiment of the present invention is directed to a system for generating and displaying a presentation describing a recommended course of treatment for a patient. The system includes at least one computer. The at least one computer includes at least one memory device, a healthcare desktop application stored in the at least one memory device and a presentation tool stored in the at least one memory device. The system also includes means for selecting a presentation template for a presentation. The presentation template includes at least one slide being configured for display by the presentation tool. In addition, the system includes means for incorporating at least one slide having information on at least one healthcare procedure included in a recommended course of treatment for a patient into the presentation template to generate an intermediate presentation. The intermediate presentation includes a plurality of slides being configured for display by the presentation tool. Further, the system includes means for incorporating patient specific healthcare information from the healthcare desktop application into the plurality of slides of the intermediate presentation to generate a final presentation including a plurality of slides being configured for display by the presentation tool. Finally, the system has means for storing the final presentation in the at least one memory device.

One advantage of the present invention is that it integrates and exchanges information between the healthcare desktop application and the presentation software program, thereby automating and improving the process of selling or explaining the recommended treatment course.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

FIG. 2 illustrates a window used for the selection of treatment procedures for inclusion in a case presentation.

FIG. 4 illustrates sample pages or slides that are included in procedure information files.

Whenever possible, the same reference numbers will be used throughout the figures to refer to the same parts.

DETAILED DESCRIPTION OF THE INVENTION

Figure 1:
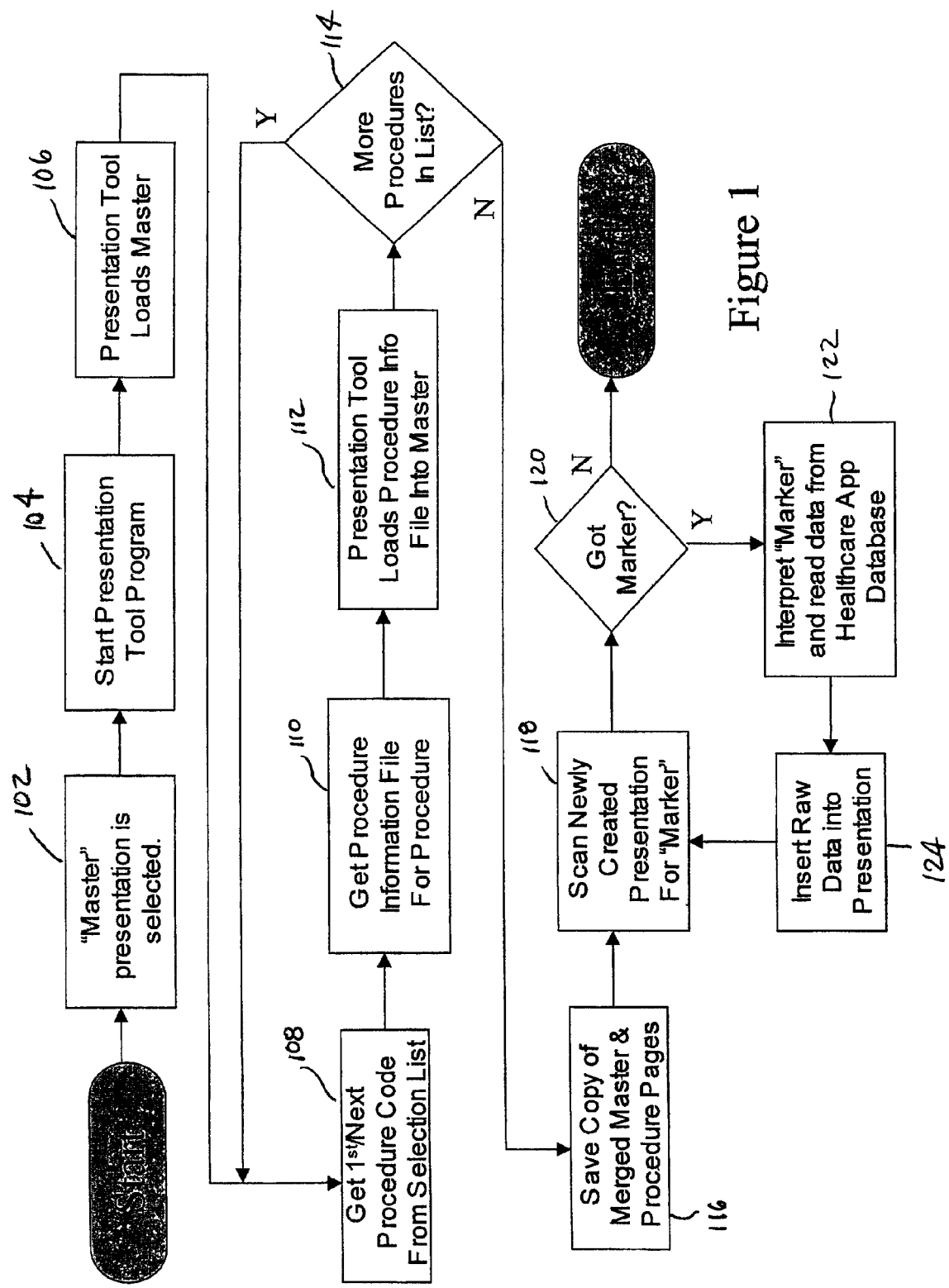
FIG. 1 illustrates a flowchart of the procedure for generating a case presentation for a patient.

FIG. 1 illustrates the steps in a preferred embodiment of the present invention that permits a user, with a single action such as a mouse click, to generate and possibly show a complete case presentation that describes recommended healthcare procedures for a given patient using information specific to that patient's healthcare record. The patient's healthcare record is usually stored in a database of a healthcare desktop application. The healthcare desktop application is preferably a dental practice management software application, however any type of practice management software for a healthcare profession can be used. The presentation that is created for the patient is generated in a format that permits the presentation to be shown to the patient using a presentation tool or software program. The presentation tool or software program is preferably a slide-based presentation tool or software program such as Microsoft PowerPoint or StarOffice Impress from Sun Microsystems, however any type of presentation tool or software program can be used.

Both the healthcare desktop application and the presentation tool are designed for execution on any type of general purpose computer or computer network having memory devices (e.g. RAM, ROM, hard disk, CD-ROM, etc.), processing units (e.g. CPU, ALU, etc.) and input/output devices (e.g. monitor, keyboard, mouse, printer, etc.).

In a preferred embodiment of the present invention, the healthcare desktop application is a dental practice management application. In the following description of the preferred embodiments the references to the healthcare desktop application may be in the context of a dental practice management software application. However, it is to be understood that any healthcare practice management application can be used and the references to dental specific items e.g. procedures and terms, would be modified or changed to correspond to specific items of the specific field of healthcare that relates to the healthcare practice management application.

Before starting the process of generating a presentation as shown in FIG. 1, the user selects the healthcare procedures for the patient that form the basis for most of the content of the presentation. FIG. 2 illustrates a window or dialog box 200 from a healthcare desktop application that displays a list of proposed procedures 202 to be performed on a patient. The list of proposed procedures 202 is generated from healthcare procedures that have been previously identified by a healthcare provider as being needed by the patient. The list of proposed procedures are also preferably identified by their corresponding billing codes from the governing body. The user then selects the healthcare procedures from the list 202 that are to be included in the presentation to the patient. Upon selection of the healthcare procedures, an indicator 204 is displayed in the list 202 that identifies the selected procedures. The indicator 204 informs the use that the corresponding healthcare procedure has been included in a presentation generated for the patient.

In another embodiment of the present invention, all pending procedures for a patient stored in the healthcare desktop application can automatically be selected for inclusion in the presentation to the patient. In this embodiment, the user can begin the single action process for generating a presentation for a patient without having to select the procedures to be included in the presentation. The automatic selection of all procedures can simplify the process for generating a presentation and permit the user to more quickly generate a presentation for a patient.

After the healthcare procedures to be included in the presentation have been selected, the process shown in FIG. 1 is started to generate a presentation for a patient. The process can be started by selecting a button from a toolbar displayed in the healthcare desktop application, e.g. a "Build Presentation" button, or by selecting a menu option from a menu included with the healthcare desktop application, e.g. a "Build Presentation" menu option. However, any other similar type of action such as a keyboard command can also start the process shown in FIG. 1. The selection of the "Build Presentation" button or menu option is the single action on that starts the process of generating a presentation for a patient.

Figure 3:
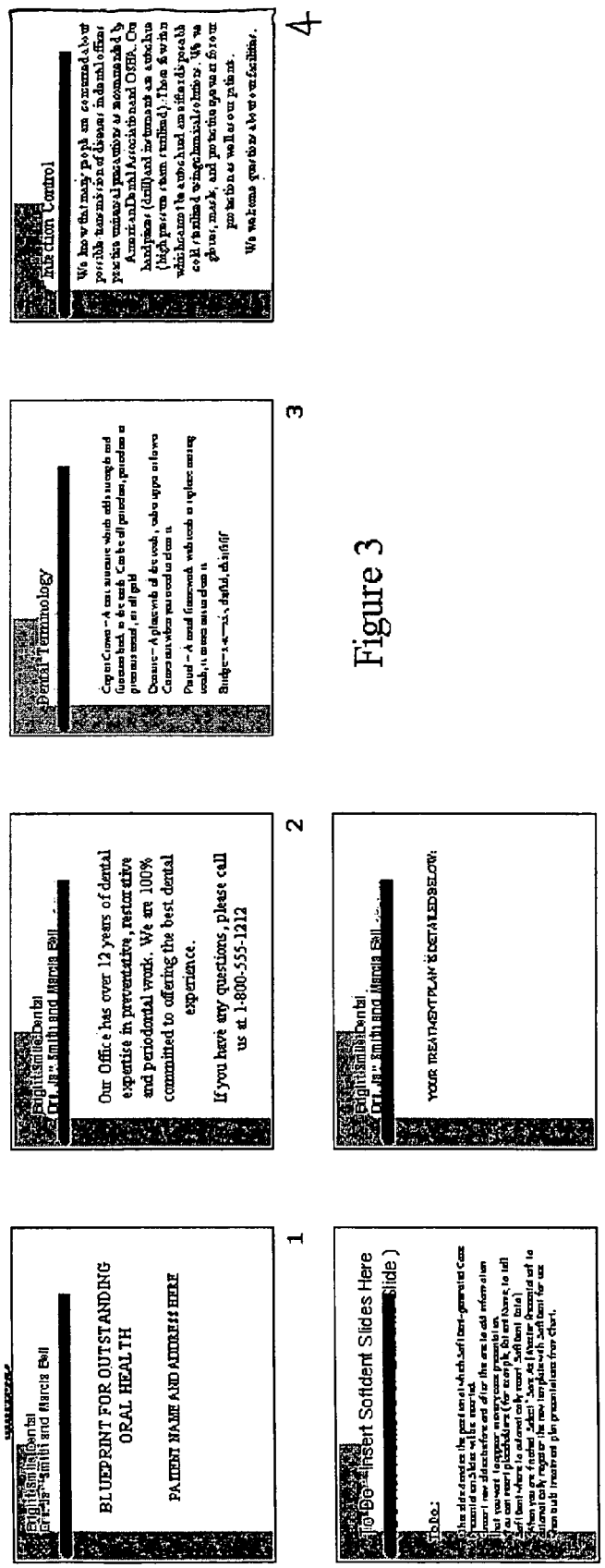
FIG. 3 illustrates sample pages or slides that can be included in a Master template.

Referring back to FIG. 1, a "Master" is selected by the system in step 102. The Master is a template used for constructing the presentation and serves several purposes. First, the Master includes general information that the user wants to show to a patient in every presentation. Examples of this type of general information can be the dental practice name and address, the list of providers in the practice, the list of specialties or services offered by the practice, a description of infection control procedures, general payment policies or any other similar type of background or non-patient specific information. Second, the Master designates a common look or theme for the presentation. The look or theme of the presentation may be a color scheme or business logo. Third, the Master presents common information in a consistent manner on every presentation, thereby reducing the chance for errors or misinformation. Also, having a Master presentation template makes it very simple to implement changes for all presentations by only having to make the change in the Master presentation template. For example, if the healthcare office needs to change its hours of operation, the user would modify the hours of operation included in the Master presentation template and then any subsequently generated presentation would have the new hours of operation. Most importantly, the Master controls the order of the information in the presentation and reduces the possibility of errors in presenting the information to the patient. FIG. 3 illustrates a sample Master template that has six pages. As part of the single action process, e.g. one click of the mouse, the Master is selected automatically by the healthcare desktop application and can be thought of as a type of default Master template. However, in another embodiment of the present invention that is described later, the user is permitted to select from multiple Master presentation templates, choosing the one that is best suited for the given patient and/or situation.

In step 104, the healthcare desktop application starts the presentation tool. The presentation tool can preferably be started as a background application, with little or no knowledge by the user that the presentation tool has been started by the healthcare desktop application. However, the healthcare desktop application can start the presentation tool in other known manners. In step 106, the selected Master presentation template is loaded into the presentation tool. A command from the healthcare desktop application preferably directs the presentation tool to accomplish the loading of the selected Master presentation template into the presentation tool. In step 108, the healthcare desktop application obtains a selected healthcare procedure from the list of selected healthcare procedures. The healthcare desktop application obtains a procedure information file that corresponds to the obtained selected healthcare procedure in step 110. Preferably, the procedure information file is associated with the corresponding billing code for the procedure.

Procedure information files are stored in the memory devices of the computer or network and are in the same format as the Master presentation template, i.e. a format understood by the presentation tool or software program. A separate procedure information file exists for most healthcare procedures in a particular discipline (e.g. there is one file for each ADA procedure code). A procedure information file preferably includes one or more procedure in formation pages or slides that have information on a particular procedure and may include text, pictures, charts, multimedia (.AVI files), sound (.WAV files), animation or other information in any form supported by the presentation software program. FIG. 4 illustrates two sample pages that may be included in procedure information files. Another embodiment of the present invention that is described later allows the user to customize a Master presentation template or the pre-configured procedure information pages in the procedure information files.

Next, in step 112, the procedure information pages from the procedure information file that is associated with the selected procedure are inserted into the Master presentation template at the appropriate place, if and only if the procedure information pages for the selected procedure have not been previously inserted into the Master presentation template. If a certain procedure is included multiple times in the list of selected procedures, only one set of procedure information pages associated with the procedure is preferably inserted into the presentation. The procedure information pages are preferably inserted into the Master presentation by the presentation tool. Preferably the Master template loaded into the presentation tool includes an indicator or flag that informs the presentation tool where to insert the procedure information pages from the procedure information file. An example of an indicator in the Master template is illustrated in page 5 of FIG. 3. Page 5 of FIG. 3 is the page in that sample Master template that informs the healthcare desktop application where to insert the procedure information pages into the Master template. A page similar to page 5 is required in all Master templates to permit procedure information pages from the procedure information files to be inserted into the Master template. The page in the Master template with the indicator is preferably not displayed to the patient, only the procedure information pages inserted into the presentation at the indicator. Together, the Master presentation template and the procedure information pages form the basis for the presentation on the recommended course of treatment. In step 114, the healthcare desktop application checks the list of selected procedures to see if there are any more selected procedures. If there are more selected procedures in the list of selected procedures the process is returned to step 108, and another procedure information file is loafed into the Master presentation template, as described above with regard to steps 110-114. If there are no more selected procedures to be included in the Master presentation template, the Master presentation template with the merged procedure information pages is saved in step 116.

The merging of the Master presentation with the procedure information pages from the procedure information files for all selected procedure codes is done using a process known as Automation. Automation is a process whereby a software component makes available sortie or all of its data and functionality to other independent software components. Automation allows the healthcare desktop application to control the presentation software program, telling it how to construct the presentation. After the procedure information pages from the procedure information files are merged with the Master presentation, a copy of the newly combined presentation is saved in a file on the computer or network in step 116. This saved copy is the presentation for the planned course of treatment for that patient on that date, and is integrated into the patient's clinical record included in the healthcare desktop application.

Next, information specific to the patient is added to the newly created presentation. The adding of patient specific information is begun by automatically scanning the newly created presentation for Placeholders or Markers in step 118. The presentation software program preferably identifies any Placeholders in the newly created presentation. The Placeholders, which are recognized and operational only when used in conjunction with the healthcare desktop application, designate where and how to input the case specific information from the healthcare desktop application in the newly created presentation. In other words, Placeholders are merely indicators in the pages of the Master template or the procedure information files where case specific information is to be inserted into the presentation.

Figure 7:
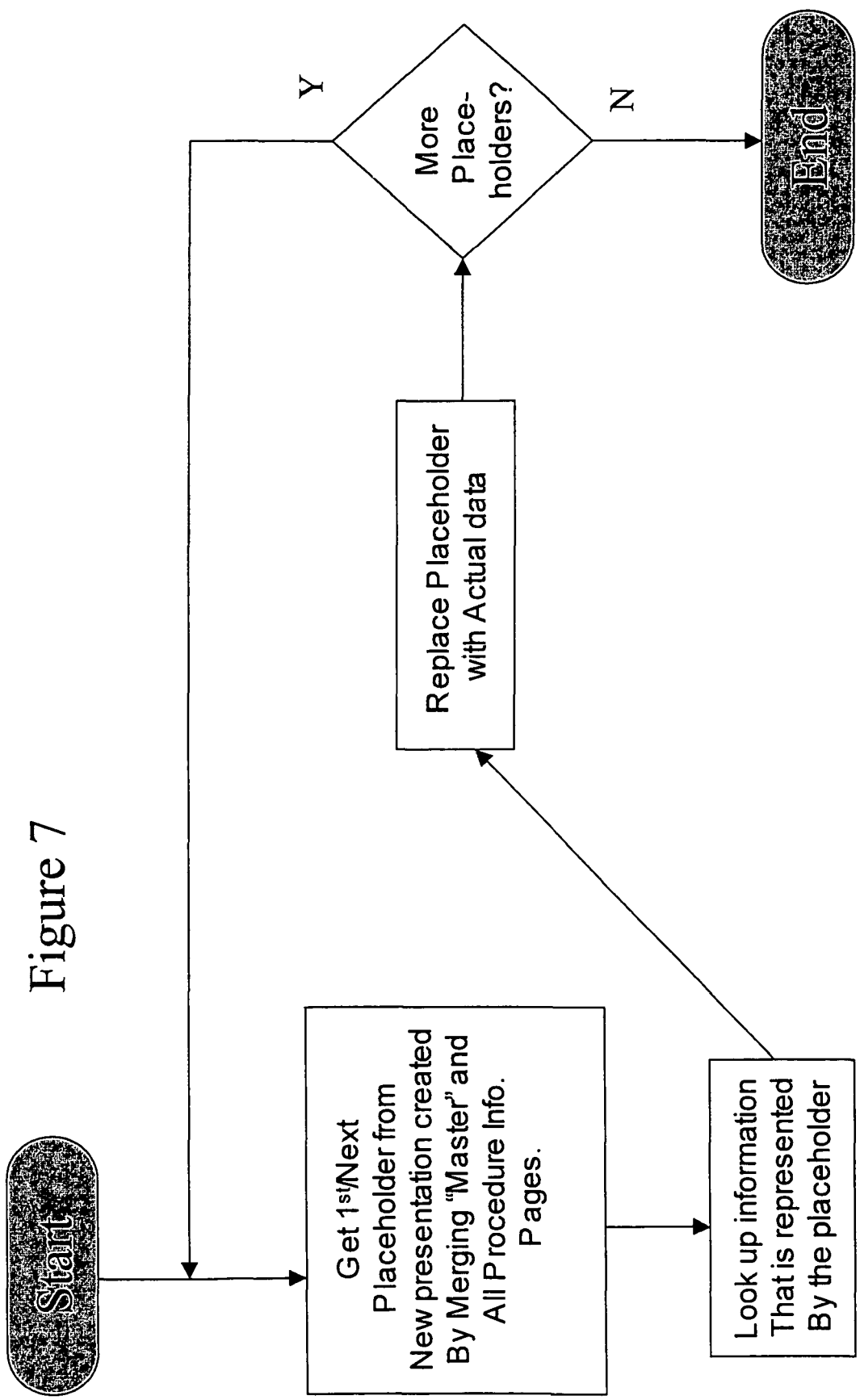
FIG. 7 illustrates a flowchart of the procedure for replacing Markers in the presentation.

In step 120, a check is made to see if a Marker has been located in the newly created presentation. If a Marker has been located, the healthcare desktop application interprets the Marker and gathers the appropriate information from the database of the healthcare desktop application in step 122. The presentation software program then receives the corresponding information from the healthcare desktop application and inserts the information in place of the Marker in step 124. After inserting the information in place of the Marker in step 124, the presentation software program returns to step 118 and scans the newly created presentation for another Marker or Placeholder. FIG. 7 illustrates a flowchart describing an alternate process of replacing the Placeholders with data from the healthcare desktop application in the newly created presentation that is similar to steps 118-124 of FIG. 1.

Figure 6:
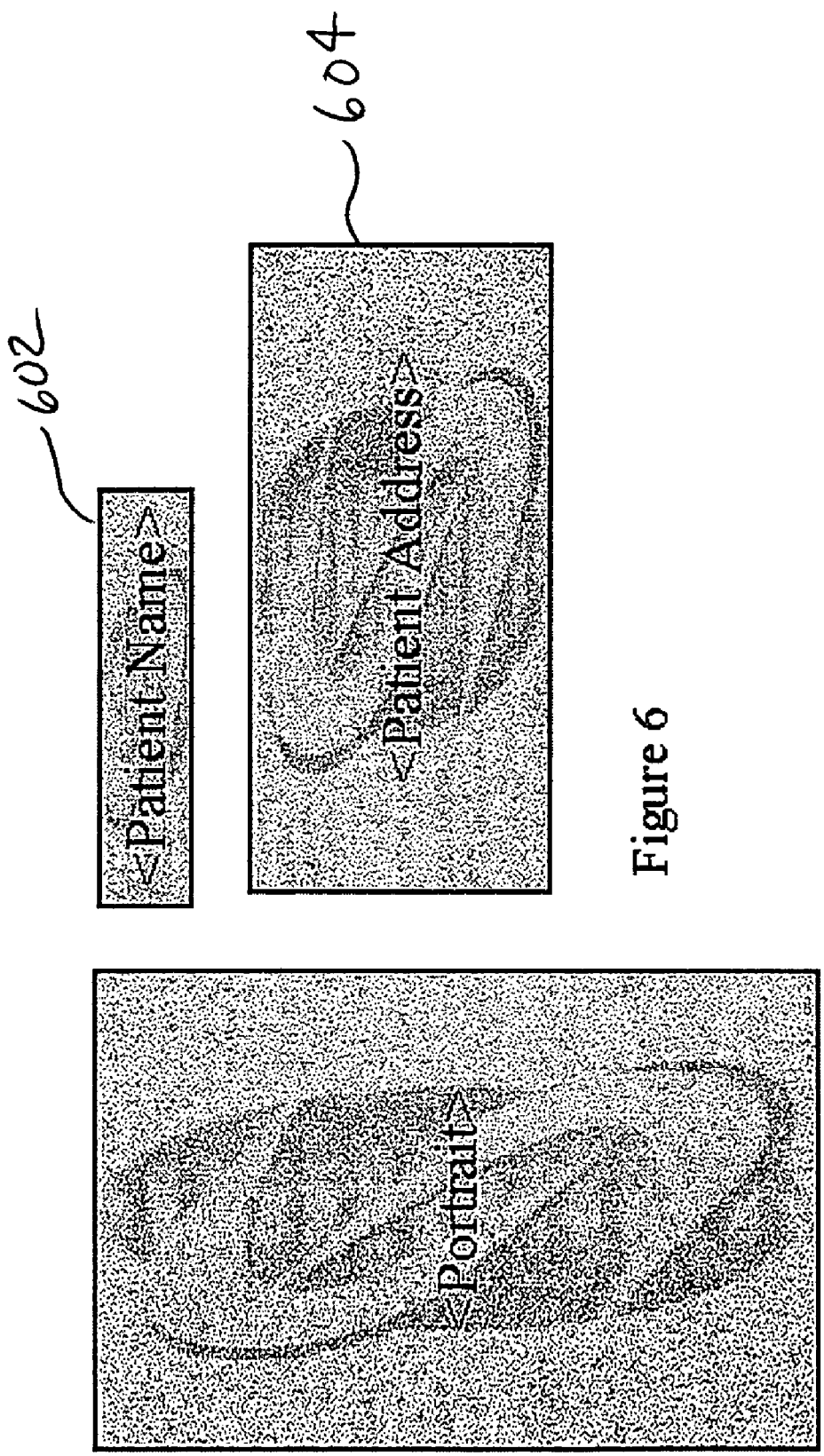
FIG. 6 illustrates sample Placeholders that can be included in a presentation.

FIG. 6 illustrates several sample Placeholders that could be included in a page or slide of the newly created presentation. Each Placeholder identifies some specific piece of information about the patient, practice, or provider, or any other information stored in the database of the healthcare desktop application. For example, Placeholder 602 would indicate that the patient's name (obtained from the healthcare desktop application) is to be inserted into the presentation at the location of the Placeholder 602. The same applies for Placeholder 604 with regard to the patient's address. The specific information, whether it relates to the patient, provider, practice or other information, is gathered through a data exchange process between the healthcare desktop application and the presentation software program, in real-time. It is important to exchange data between the two disparate software applications in real-time to permit the most up-to-date and accurate information to be inserted into the newly created presentation. Another embodiment of the present invention that is described later relates to the setting up and customizing of the Placeholders in the Master or in the procedure information pages.

In another embodiment of the present invention, if the corresponding information relating to a Placeholder cannot be located by the healthcare desktop application or does not exist in the healthcare desktop application, the Placeholder is left in the presentation and the process is continued at step 118. The user can then either insert the information manually or delete the Placeholder, both of which are described below. Alternatively, an error message can be presented to the user when the corresponding information of a Placeholder cannot be located.

After all Placeholders are replaced with actual data and no more Placeholders are located in step 120, the presentation is complete and ready for viewing. The single action process is completed by permitting the user to view or customize the presentation. Once the single action process is completed, the user can show the completed presentation to the patient using the presentation tool.

In another preferred embodiment of the present invention, the user may elect to have multiple Master presentations. The use of multiple Master presentations may be either necessary or desirable to a given healthcare practice. One example of the use of multiple Master presentations or templates is to have a different presentation for an insured patient versus a non-insured patient. Another example is to have a different presentation for each provider in the practice. A third example is to have a different presentation for a parent of a child patient versus an adult patient. In these situations, or in any other situation where the user wants multiple Master presentations, the user must then chose the Master presentation template for each case presentation that is constructed. The use of multiple Master templates would change step 102 in FIG. 1 to prompt the user to select the Master template the user desires to use as the basis for his/her presentation instead of the healthcare desktop application selecting the Master template. A default template can also be designated, if the user does not know which Master template to use for generating a presentation.

Figure 8:
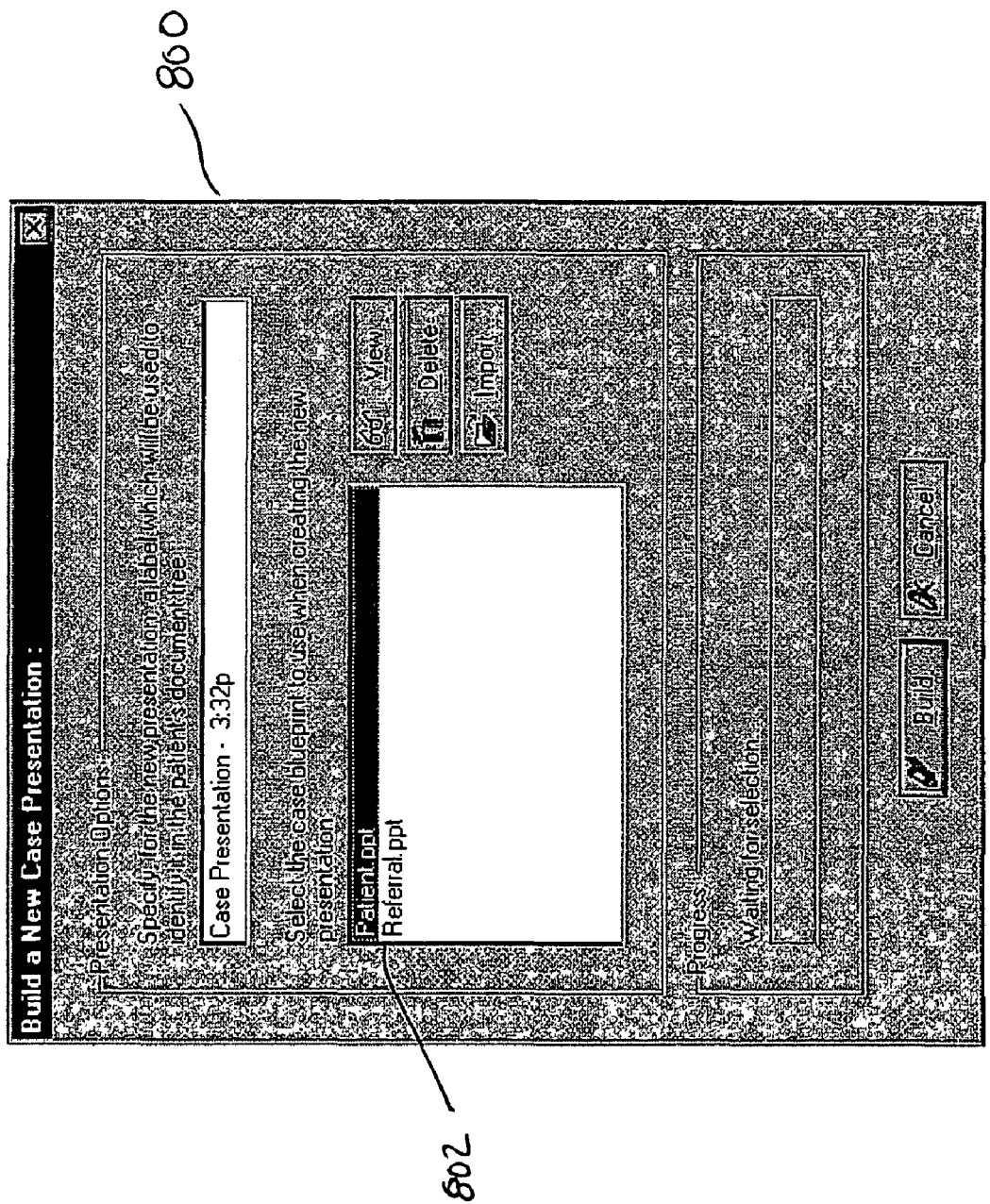
FIG. 8 illustrates a window for the selection of a "Master" presentation template.

FIG. 8 illustrates a sample window or dialog box 800 from the healthcare desktop application that can be used for selecting the Master template or blueprint. The user can select the Master template to be used from a list of Master templates 802. In addition, the user has other options available with regard to the selection of a Master template. The user can preview the layout of the Master template to decide if the selected Master template is the correct one. In addition, the user can load or import another Master template from outside of the healthcare desktop application and use that one instead of the Master templates presented in the list of Master templates 802.

Figure 9:
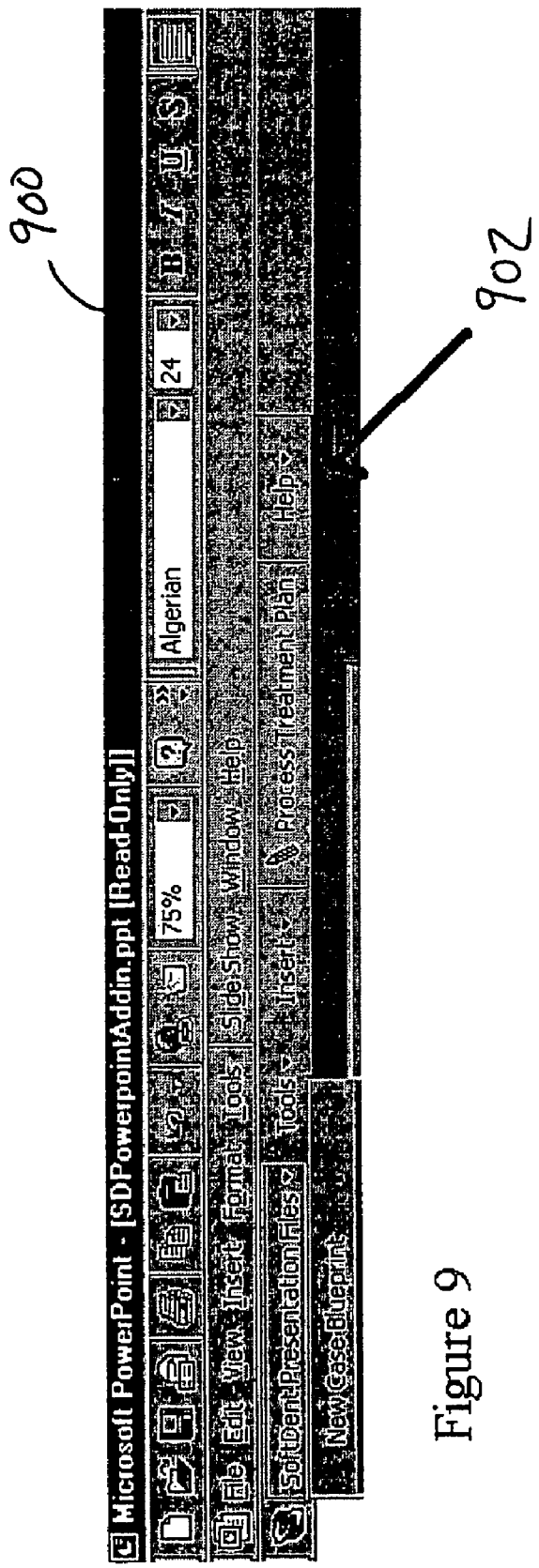
FIG. 9 illustrates a partial view of a presentation tool with an add-in tool bar.

In another preferred embodiment of the present invention, the user can customize the Master presentation templates through the use of an add-in tool bar that appears in the presentation software, but is designed and programmed for use with the healthcare desktop application. FIG. 9 illustrates a partial view of the presentation tool 900 that includes the add-in tool bar 902. However, in order to use the add-in tool bar 902, the presentation tool or software program must be configured to accept a software plug-in or add-in component. Some common methods for implementing an add-in component are as an Active-X extension or control, or as a V.3A (Visual Basic for Applications) macro, although other similar methods can be used for implementing an add-in component. The healthcare application interface plug-in tool bar 902 adds functionality to the presentation software program, essentially linking the healthcare desktop application and the presentation software program by enabling data to be exchanged and functionality to be shared between them.

Figure 10:
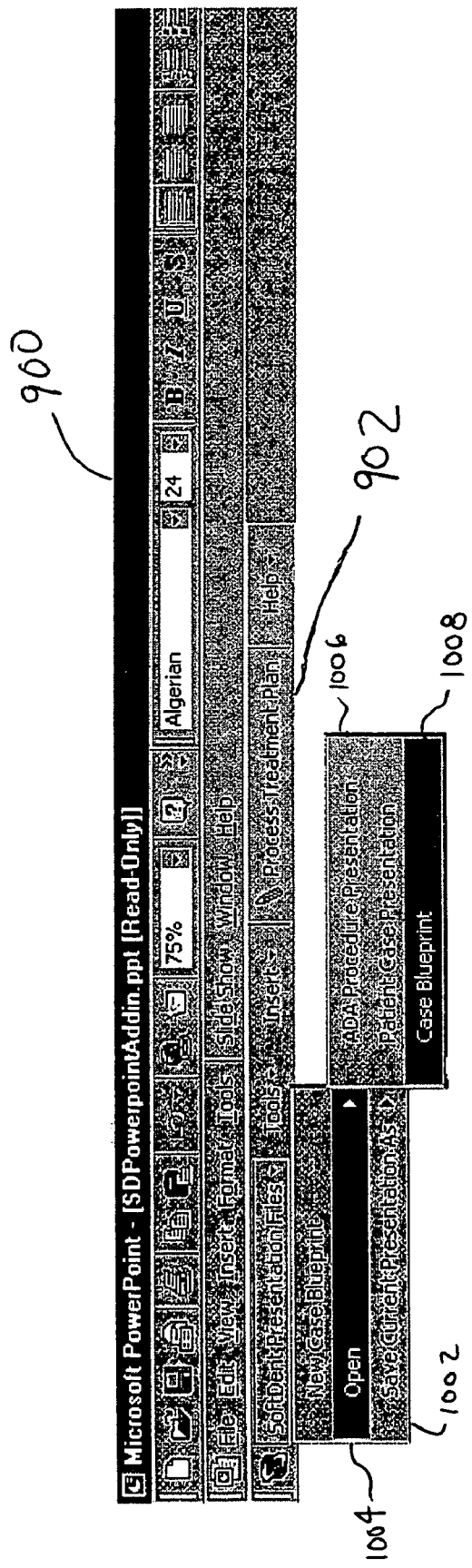
FIG. 10 illustrates an expanded view of the add-in tool bar for opening a "Master" presentation template for customization.
Figure 11:
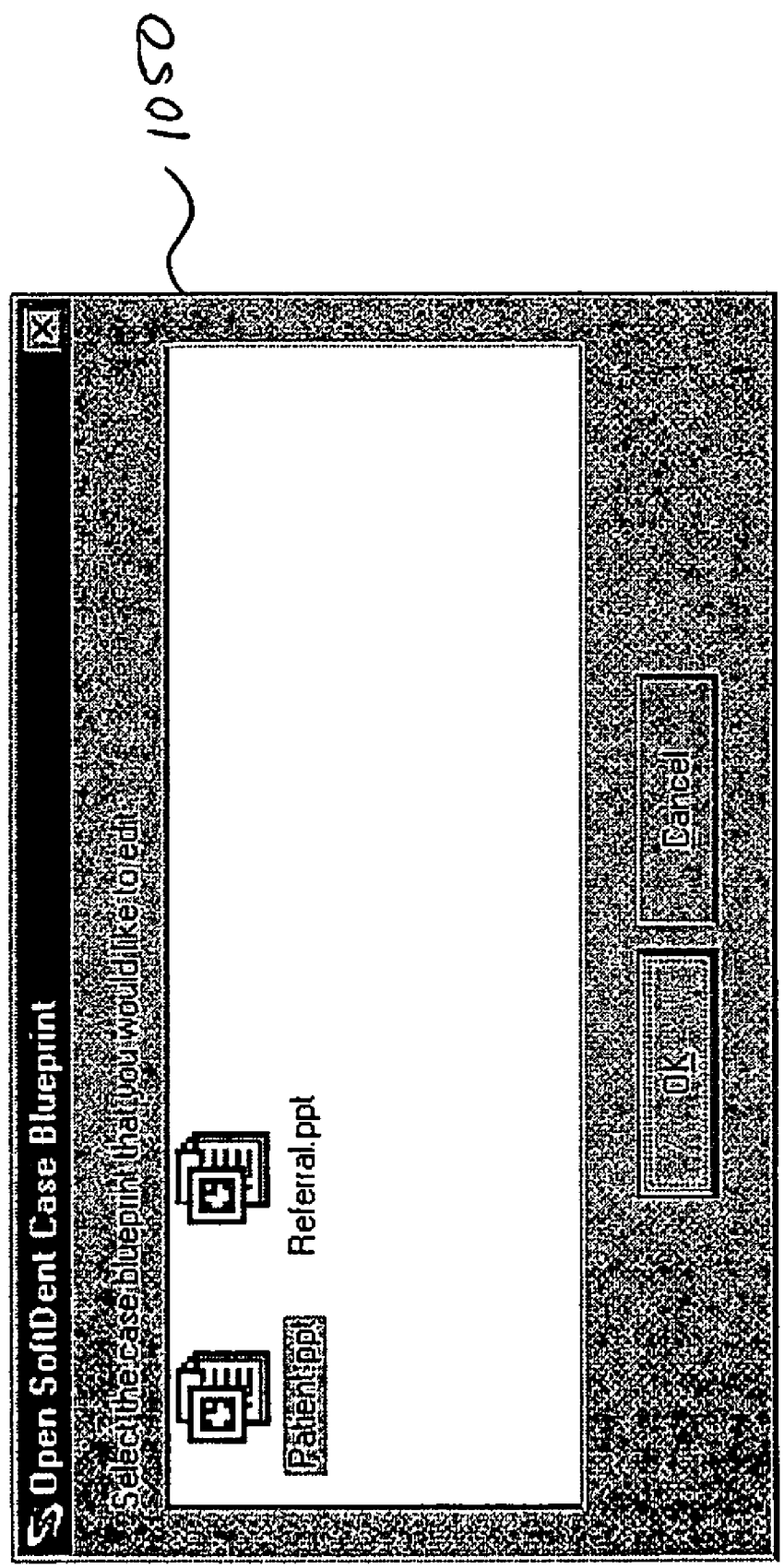
FIG. 11 illustrates a window for selecting the Master template for customization.

To customize a Master presentation template the user starts by opening a Master presentation template for editing. FIG. 10 illustrates one way of utilizing the healthcare application interface add-in tool bar 902 for opening a Master presentation template for editing. The user selects an option in the toolbar that presents a pop-up window 1002 with an "Open" command 1004. The selection of the "Open" command 1004 results in another pop-up window 1006 being displayed where the user can select the "Case Blueprint" menu option 1008 that displays to the user the Master templates or blueprints available to the user for editing. Once the user selects the Case Blueprint menu option 1008, the user is presented with a selection window or dialog box 1050 shown in FIG. 11 to select a Master template for customization.

Once the user selects a Master template from the dialog box 1050, the selected Master template is opened and displayed in the presentation software program. The user can then select a slide or page of the Master template for customization, whereby elements of the presentation can be added, deleted or changed and then saved, as needed, using either the capabilities and functionality provided through the healthcare application interface add-in tool bar 902 or included in the presentation software program 900. In addition, Placeholders can be inserted into, or deleted from, the Master presentation to provide more customization capability, by selecting the appropriate menu option from the healthcare application interface add-in tool bar 902. When a Placeholder insertion type of customization is selected through the healthcare application interface add-in tool bar 902, a Placeholder object is created and inserted onto the slide of the Master template. For example, to include the patient's picture on a slide, select the Insert, Placeholder, Portrait commands (not shown) from the healthcare application interface add-in tool bar 902. The Portrait Placeholder is inserted on the slide and can be resized or positioned as necessary. This process can be repeated for any number or type of Placeholders.

In another embodiment of the present invention, the user can create a new Master template by selecting appropriate menu options from the healthcare application interface add-in tool bar 902. The user can add in any type of pages that the user desires. However, the user must include a page similar to page 5 in FIG. 3 that includes the indicator to the healthcare desktop application on where to insert the procedure information pages.

In another preferred embodiment of the present invention, the user can customize procedure information pages through the use of the healthcare application interface add-in tool bar 902 that is attached to the presentation software 900 similar to the procedure described above for customizing the Master templates. Again, to be able to customize procedure information pages, the presentation software program must accept a software plug-in or add-in component. The healthcare application interface plug-in tool bar 902 adds functionality to the presentation software program, essentially linking the healthcare desktop application and the presentation software program by enabling data to be exchanged and functionality to be shared between them.

Figure 12:
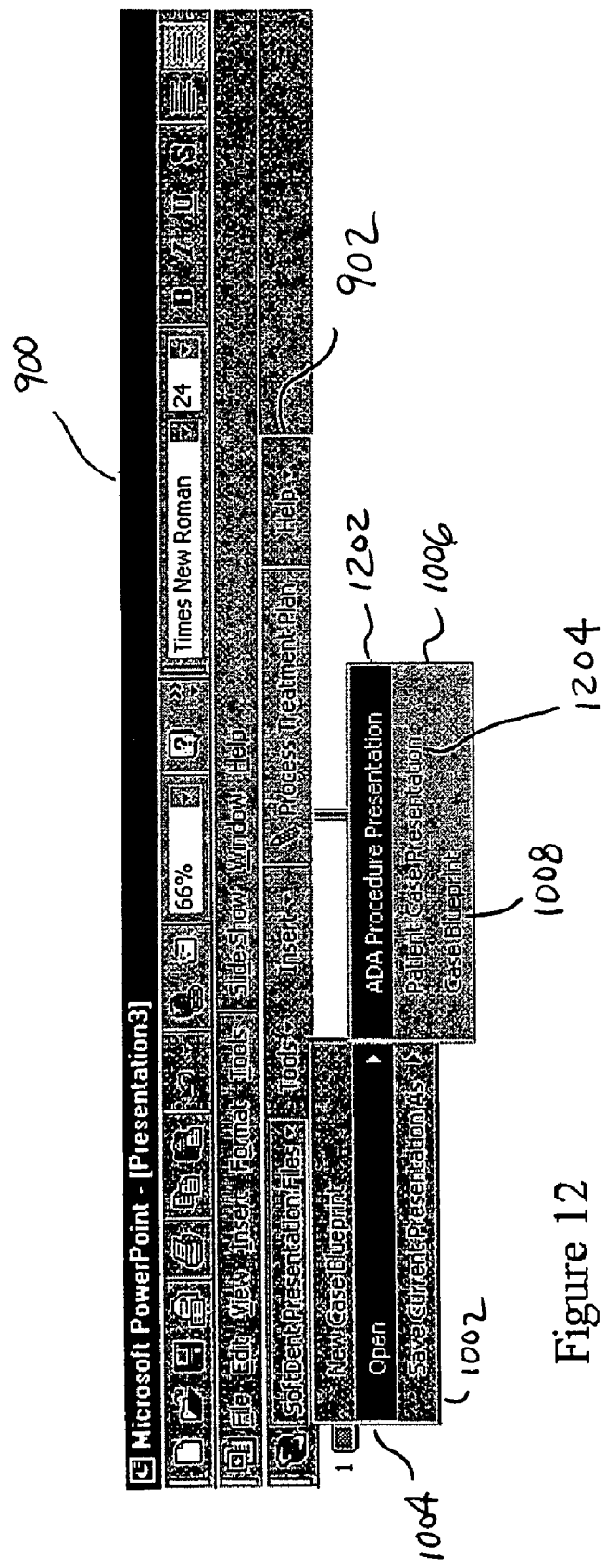
FIG. 12 illustrates an expanded view of the add-in tool bar for opening a procedure information page file for customization.
Figure 12A:
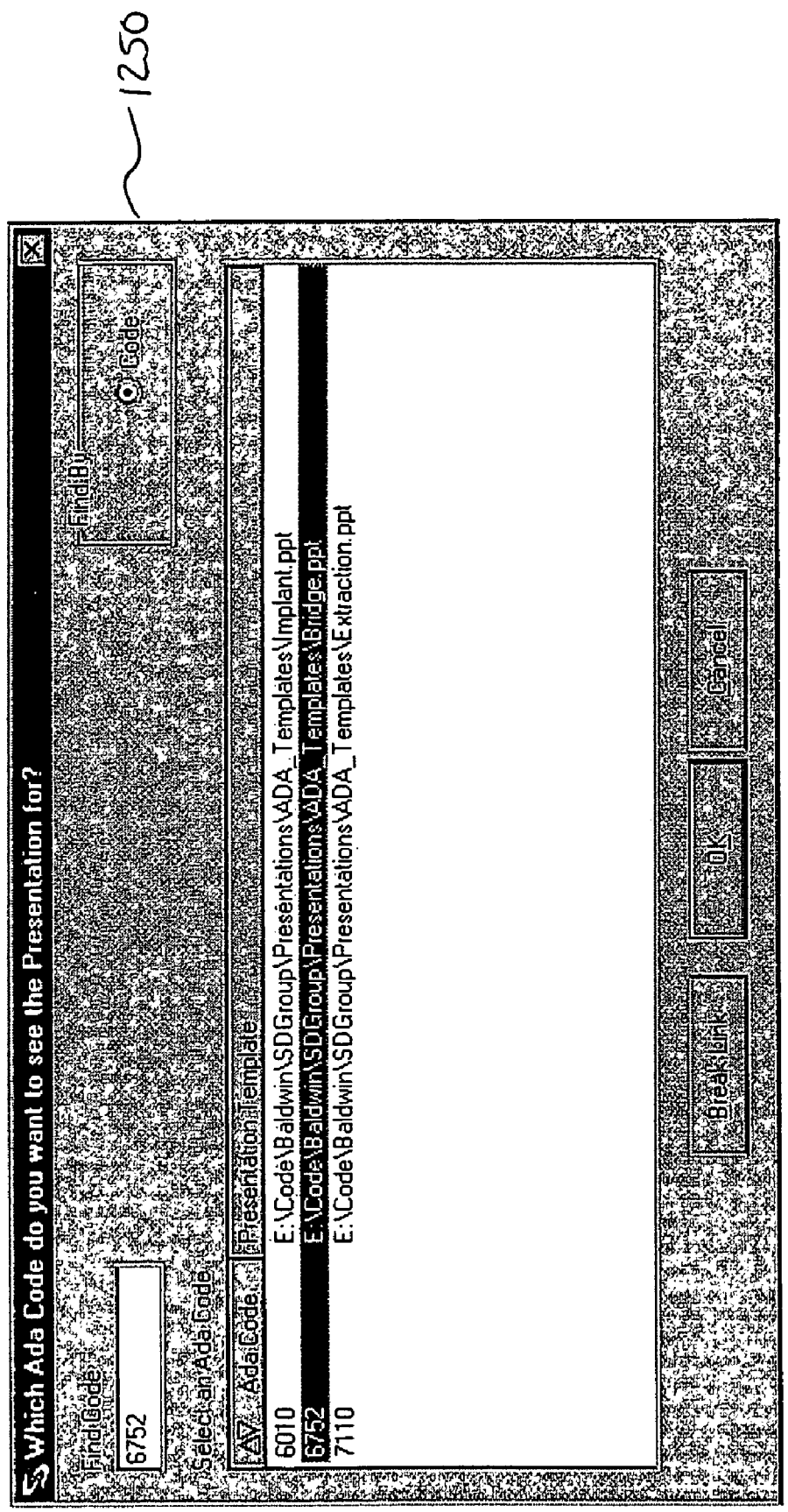
FIG. 12a illustrates a window for selecting a procedure information page.

To customize procedure information pages, the user starts by opening a procedure information file for editing. FIG. 12 illustrates one way of utilizing the healthcare application interface add-in tool bar 902 for opening a procedure information page for editing. The user selects an option in the healthcare application interface add-in tool bar 902 that presents a pop-up window 1002 with an "Open" command 1004. The selection of the "Open" command 1004 results in another pop-up window 1006 being displayed where the user can select the "ADA Procedure Presentation" menu option 1202 that displays to the user the procedure information files available to the user for editing. Once the user selects the ADA Procedure Presentation menu option 1202, the user is presented with a selection window or dialog box 1250 shown in FIG. 12*a* to select a procedure information file for customization.

After the procedure information file is opened and displayed in the presentation software, a slide is selected for customization. Elements in the presentation information file can be added, deleted or changed and then saved, as needed. In addition, Placeholders can be inserted into, or deleted from, the procedure information pages to provide more customization capability, by selecting the appropriate menu option from the healthcare application interface add-in tool bar 902. When a Placeholder insertion type of customization is selected through the healthcare application interface add-in tool bar 902, a Placeholder object is created and inserted onto the slide. For example, to include the patient's dental chart on a slide, select the Insert, Placeholder, Patient Charts, Restorative Charts, Current commands (not shown) in healthcare application interface add-in toolbar 902. The Current Chart Placeholder is inserted on the slide and can be resized or positioned as necessary. This process can be repeated for any number or type of Placeholders.

Another embodiment of the present invention relates to the variety and accessibility of the information that is available for insertion into the presentation. Through the use of Automation, a data exchange process has been put in place that allows the healthcare application program to access and/or exchange data with the presentation software program, despite the fact that they are both separate, independent software components. This data exchange is the key to the building of a case presentation based on the specific patient, the current diagnosis, and planned course of treatment. The data exchange process can include any information and essentially is only bound by what information is stored by the healthcare desktop application. Information is inserted in one of two ways. The first way is through the use of Placeholders, whereby the information is read and placed into the presentation during the creation phase of the presentation. At this time, all Placeholders are replaced with the actual data taken from the healthcare desktop application database. The second way is by direct insertion of the information into the presentation, after the process of FIG. 1 has created the presentation, but usually before the presentation is shown to the patient. The direct insertion of information provides the opportunity to provide the most detailed and specific customization to that case, as only that one patient presentation is being changed.

The direct insertion of information is accomplished using the healthcare application interface add-in tool bar 902. To directly add information to the presentation, the user starts by opening the particular presentation for editing. The user selects an option in the healthcare application interface add-in toolbar 902 that presents a pop-up window 1002 with an "Open" command 1004. The selection of the "Open" command 1004 results in another pop-up window 1006 being displayed where the user can select the "Patient Case Presentation" menu option 1204 (see FIG. 12) that prompts the user to select a patient and then a case file to open for the direct insertion of information. After the presentation is opened and displayed in the presentation software, a slide is selected by the user for customization and the insertion of information. Any element of the presentation can be changed and saved as needed. In addition, other information can be taken from the healthcare desktop application and inserted into the presentation to provide more customization capability, simply by selecting the appropriate menu options (not shown) from the healthcare application interface add-in tool bar 902. When the direct insertion of information is accomplished through the healthcare dental application interface add-in tool bar 902, actual data is retrieved from the database of the healthcare desktop application and inserted onto the slide. The information that can be inserted from the database of the healthcare desktop application may include text, pictures, charts, multimedia (.AVI files), sound (.WAV files), animation or other information that is stored in the database and supported by the presentation software program. A particular menu option in the healthcare application interface add-in tool bar 902 can be used to perform this task. For example, to include the patient's dental chart on a slide, select the Insert, Patient Data, Images, Patient Charts, and Restorative Chart commands (not shown) from the healthcare application interface add-in tool bar 902. The current restorative chart for that patient is inserted on the slide and can be resized or positioned as necessary. This process can be repeated for any number or type of data stored in the healthcare desktop application such as the patient's insurance carrier. In addition, the user can also add other information to the presentation, remove information from the presentation or change information in the presentation.

Figure 13:
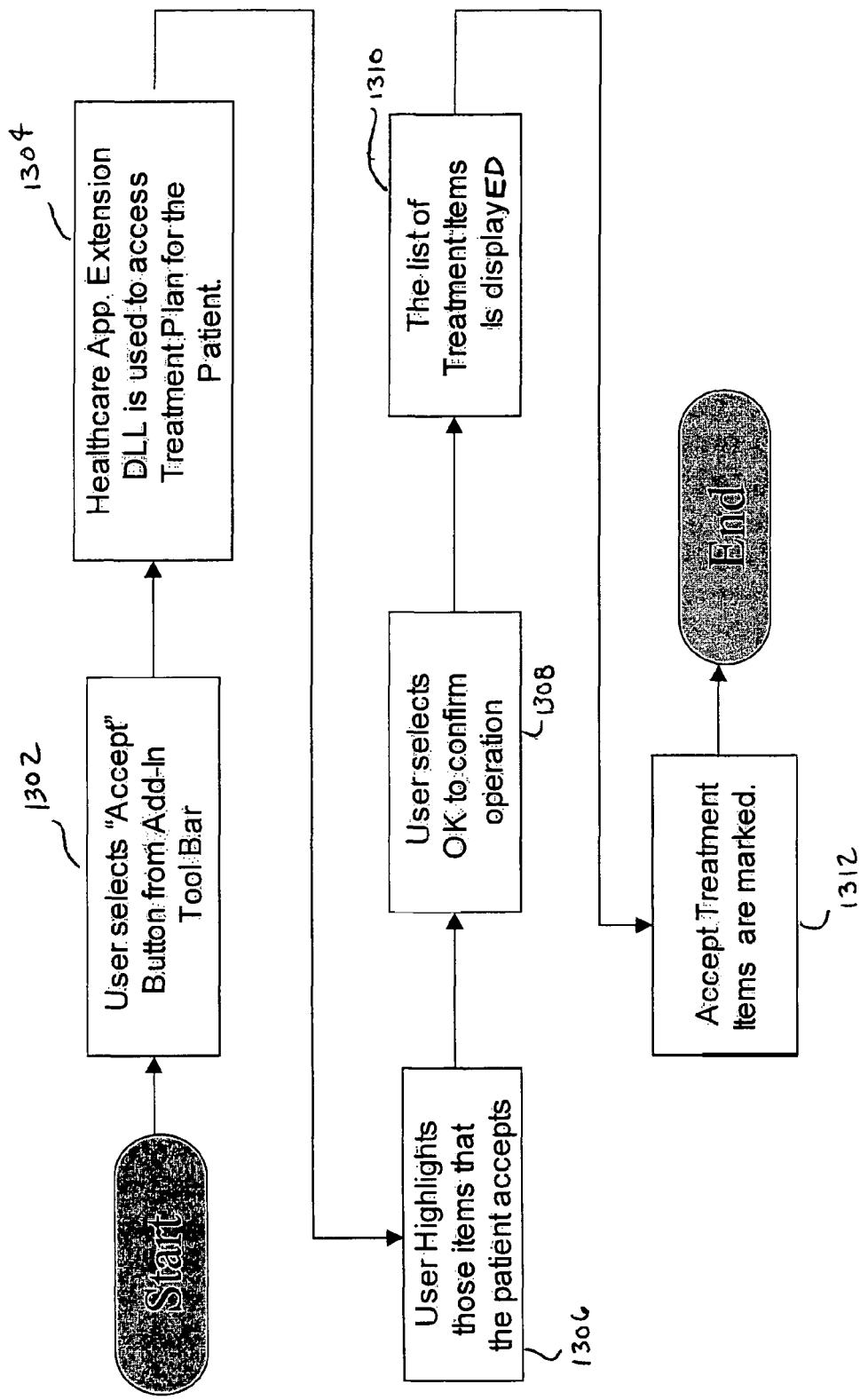
FIG. 13 illustrates a flowchart of the procedure for marking treatment items as accepted by the patient.

In another preferred embodiment of the present invention, the user has the ability to mark some or all of the recommended courses of treatment shown to the patient in the presentation as accepted by the patient. FIG. 13 illustrates the process of marking the patient's acceptance of recommended courses of treatment. To begin, in step 1302 the user selects an "Accept" option (not shown) from the healthcare application interface add-in tool bar 902 in the presentation software program. It is important that the Accept option is accessed from the healthcare application interface add-in tool bar 902 inside the presentation software program for two reasons.

First, the patient is most likely to agree to recommended courses treatment immediately after viewing the presentation with the presentation software program. Second, it is most efficient to have access to the acceptance functionality without leaving the presentation software program and having to return to the healthcare desktop application. However, for the acceptance functionality to operate properly the healthcare desktop application must be able to track and distinguish accepted planned treatments from non-accepted planned treatments. In step 1304, a healthcare desktop application extension dynamic link library (DLL) is called to access the treatment plan for the patient. The treatment plan for the patient can include the procedures that were included in the list of proposed procedures 202 or only the procedures from the list of selected procedures that were included in the presentation. In one embodiment of the present invention, the treatment plan for the patient is displayed to the patient with the presentation soft ware program. In step 1306, the user selects the proposed treatments that have been accepted by the patient. In step 1308, the user confirms his/her selections of accepted treatments. In step 1310, the list of treatments is displayed. In one embodiment of the present invention, the list of treatments is displayed to the patient and preferably includes those treatments that were accepted by the patient. Finally, in step 1312, the treatment items that are accepted by the patient are marked as such in the healthcare desktop application's database.

Another preferred embodiment of the present invention provides that all patient case; presentations, once created, get stored and logged into a document management system, whereby they are cataloged for easy and quick retrieval in the healthcare desktop application. The storage of all patient case presentations provides several benefits to the user. First, case presentations become a permanent part of the patient's clinical record. Second, the case presentations can easily be recalled or reviewed at a later date, for legal or other purposes.

In another embodiment of the present invention, secure access is controlled through the password and security system of the healthcare desktop application, preventing unauthorized viewing or editing of the patient's confidential clinical information.

Figure 5:
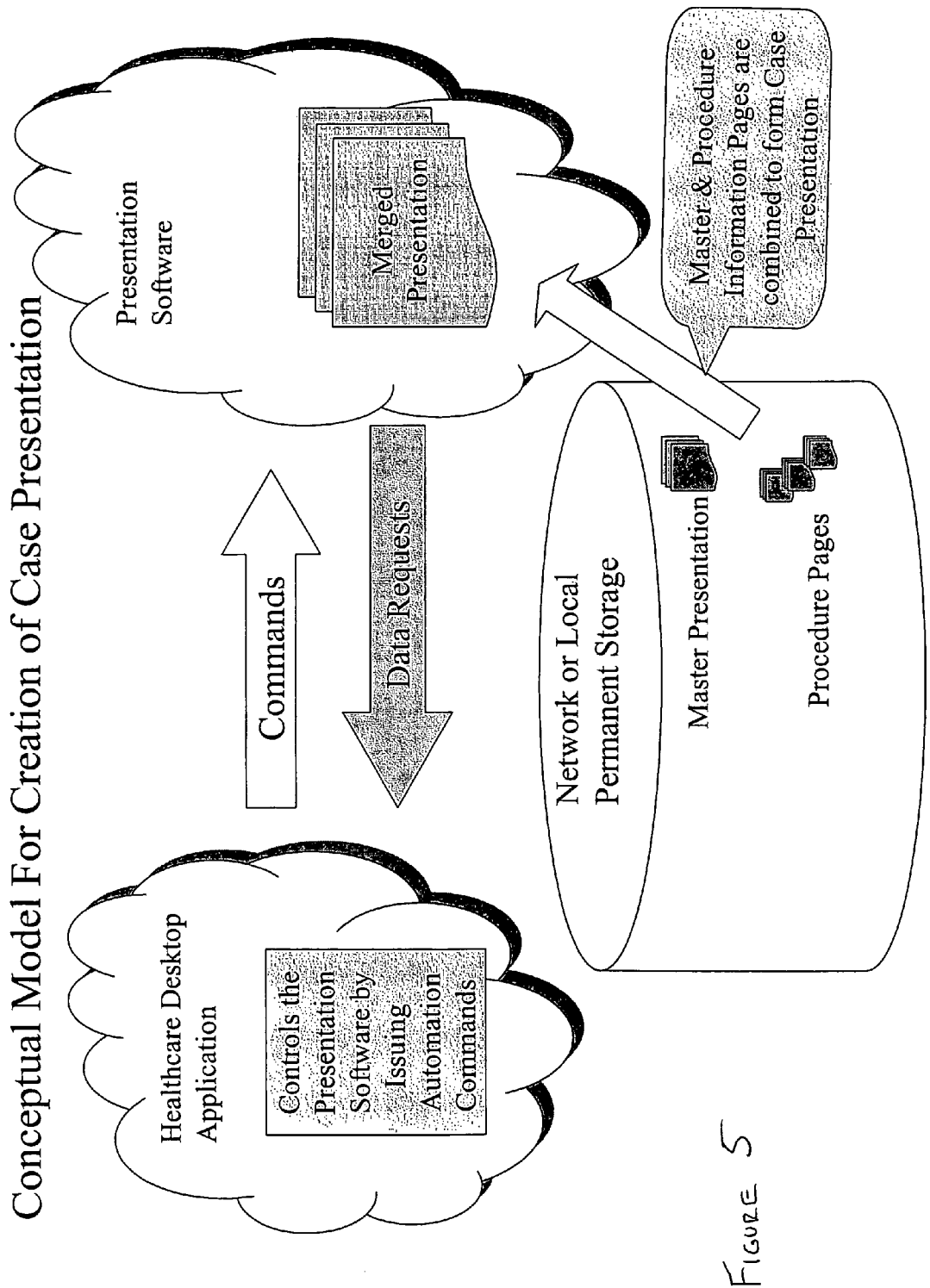
FIG. 5 illustrates a conceptual model for the creation of case presentations.

FIG. 5 illustrates a conceptual model for the creation of case presentations. As shown in FIG. 5, the healthcare desktop application interacts with the presentation software to combine the Master presentation template and the procedure information files and pages to generate a case presentation to show to a patient. The healthcare desktop application issues commands to the presentation software and the presentation software makes data requests of the healthcare desktop application to generate the case presentation for the patient.

Although the present invention has been described in connection with specific examples and embodiments, those skilled in the art will recognize that the present invention is capable of other variations and modifications within its scope. These examples and embodiments are intended as typical of, rather than in any way limiting on, the scope of the present invention as presented in the appended claims.

The invention has been described in detail with particular reference to certain preferred embodiments thereof, but it will be understood that variations

What is claimed is:

1. A method for generating and tracking presentations for a dental patient describing a recommended course of dental treatment comprising of at least one dental procedure, the method comprising the steps of:

providing and starting a presentation tool in a computer having a display;

providing at least one master template configured for display as a dental presentation on said computer display; wherein said master template: (a) includes general information to be shown in every presentation; (b) designates a common theme or look for the presentation; (c) presents common information in a consistent manner on every presentation; (d) controls the order of the information in the presentation; and (e) reduces the possibility of errors in the information presentation;

loading the dental presentation master template into the presentation tool;

providing the dental presentation master template with at least one specific dental procedure indicator for use as a point of incorporation for specific dental information on the recommended course of treatment;

inserting in each template at least one general information indicator for use as a point of incorporation for general information on the dental patient;

incorporating specific dental information about the specific dental procedure from the recommended course of treatment for the dental patient into the template, wherein incorporating specific dental information comprises the steps of i. scanning the template for a marker, wherein the marker identifies dental information specific to the dental patient and the marker identifies an insertion point in the template;

ii. retrieving dental information specific to the dental patient identified by the marker from the dental desktop application;

iii. inserting the retrieved dental information specific to the dental patient into the template a the insertion point identified by the marker; and iv. repeating the steps of scanning, retrieving and inserting for each marker in the template;

incorporating the general information on the dental patient into at least one template;

generating a dental presentation using at least one template with the incorporated specific dental information and the general information on the dental patient with one step, wherein the dental presentation is generated utilizing the computer;

storing the dental presentation in a dental desktop application on the computer;

presenting the dental presentation to the dental patient without presenting a graphic simulation of the treatment of the patient; and updating records of the individual in the dental desktop application to correspond to the indicated at least one dental procedure accepted by the individual in the presentation tool.

2. The method of claim 1, further comprising the step of initiating with a single action the steps of selecting a template, incorporating specific dental information on the recommended course of treatment on dental procedures and general information on the dental patient, and storing the presentation in a single action.

3. The method of claim 1, further comprising the step of editing the dental presentation to add additional dental procedures.

4. The method of claim 3, further comprising the steps of:

adding a plug-in tool bar to be used with the templates, wherein the plug-in tool bar enables information to be exchanged between the dental desktop application and the dental presentation; and editing the dental presentation with the plug-in tool bar.

5. The method of claim 4, wherein said step of editing the dental presentation comprises at least one of the steps of:
adding other information to the dental presentation;
removing information from the dental presentation; and
changing information in the dental presentation.

6. The method of claim 1, further comprising the steps of:
generating a list of recommended dental procedures for the dental patient, wherein the recommended dental procedures are previously entered into the dental desktop application as being recommended for the dental patient; and
selecting at least one recommended dental procedure from the list of recommended dental procedures for inclusion in the recommended course of treatment.

7. The method of claim 6, further comprising the step of using the dental desktop application to select automatically all recommended dental procedures in the list of recommended dental procedures for inclusion in the recommended course of treatment.

8. The method of claim 7, further comprising the step of editing the list of recommended dental procedures to include the dental procedure for the dental patient.

9. The method of claim 1, wherein said step of forming the template includes automatically selecting the template by the dental desktop application.

10. The method of claim 1, further comprising the step of incorporating the dental procedure into the template includes for each dental procedure, the steps of:
retrieving a procedure information file for the dental procedure, wherein the procedure information file includes a plurality of details related to the dental procedure including a member of the group comprising: test data, time for the procedure, medications for the procedure, post procedure follow up and combinations thereof; and
inserting the procedure information file into the dental template.

11. The method of claim 10, further comprising the step of editing the procedure information file prior to inserting the procedure information file into the dental template.

12. The method of claim 1, wherein the step of storing the dental presentation in the dental desktop application includes the step of integrating the dental presentation into dental desktop application records for the dental patient.

13. The method of claim 12, further comprising the steps of:
indicating at least one dental procedure of the recommended course of treatment was accepted by the dental patient; and
updating records of the dental desktop application records for the dental patient to correspond to the indicated accepted dental procedure.

14. A system for generating and displaying a dental presentation describing a recommended course of treatment having at least one dental procedure for a dental patient, the system comprising:
at least one computer, wherein said at least one computer comprises at least one memory device, a dental desktop application stored in said at least one memory device, a display, and a presentation tool stored in said at least one memory device;
a one step selection, merger and storage application for selecting a master template for a dental presentation, wherein said master template: (a) includes general information to be shown in every presentation; (b) designates a common theme or look for the presentation; (c) presents common information in a consistent manner on every presentation; (d) controls the order of the information in the presentation; and (e) reduces the possibility of errors in the information presentation; wherein the dental presentation master template is loaded into the presentation tool; and
wherein said template includes at least one slide being configured for display, wherein at least one slide comprises information on at least one dental procedure in a recommended course of treatment for a dental patient, wherein the patient specific dental information from said dental desktop application is incorporated into said plurality of slides as a dental presentation, and wherein said dental presentation is stored in said at least one memory device;
a merger application that is adapted to exchange of information between the dental desktop application and the template, wherein the merger application comprises:
i. a scanner for scanning in information; and
ii. at least one marker for identifying dental information specific to the dental patient and the marker identifying an insertion point into the dental presentation for the dental information specific to the patient; and wherein the merger application retrieves dental information specific to the patient identified by the marker from the dental desktop application; and the merger application inserts the retrieved dental information specific to the patient into the insertion point identified by said marker;
a presentation tool for presenting said dental presentation to said dental patient without presenting a graphic simulation of the treatment of the patient; and
a tracking tool, wherein when at least one dental procedure of said recommended course of treatment is accepted by a dental patient in the patient records in the dental desktop application correspond to the accepted dental procedure.

15. The system of claim 14, wherein the selection, merger, and storage application in a single action further incorporates general patient information into the dental presentation.

16. The system of claim 14, wherein the presentation tool further comprises:
a program for creating a presentation;
an editor for modifying a presentation; and
a tool for displaying the presentation.

17. The system of claim 14, further comprising
a plug-in tool bar for enabling an exchange of information between the dental desktop application and the dental presentation; and
an interface for the editor for modifying, adding, or changing information in the dental presentation using the plug-in tool bar.

18. The system of claim 14, wherein said dental desktop application comprise an automatic selection system for the template.

19. The system of claim 14, further comprising:
a list generation program for generating a list of recommended dental procedures for the dental patient from a list of recommended dental procedures having entered into said dental desktop application for the dental patient; and
selection criteria for selecting certain dental procedures from the list of recommended dental procedures for inclusion in said recommended course of treatment.

20. The system of claim 19, wherein the dental desktop application automatically selects all recommended dental procedures in said list of recommended dental procedures for inclusion in said recommended course of treatment.

21. The system of claim 14, further comprising an indicator configured to indicate a point of incorporation for at least one slide having specific dental information on at least one dental procedure included in a recommended course of treatment.

22. The system of claim 14, further comprising a plug-in tool bar, wherein said plug in toolbar facilitates an exchange of information between said dental desktop application and the dental templates.

23. The system of claim 14, further comprising a list of dental templates in said dental desktop application and a program for selecting the dental template from said displayed list.

24. The system of claim 14, wherein the information on at least one dental procedure comprises:
   instructions for obtaining a dental procedure included in said recommended course of treatment; and
   a program to retrieve a procedure information file for the dental procedure, wherein the procedure information file comprises information on said dental procedure and insert the procedure information file into the dental template.

25. The system of claim 14, further comprising:
   an editor for editing information on the dental procedure in said procedure information file.

26. The system of claim 14, wherein the dental presentation stored in the at least one memory device comprises an integrator for integrating said dental presentation into dental desktop application records for said dental patient.

27. The system of claim 26, wherein said dental presentation incorporates information from a dental database on at least one of a name and address of a dental practice, a list of services offered by said dental practice, a description of infection control procedures and general payment policies.

28. The system of claim 27, wherein:
   said dental desktop application comprises a database, said database including clinical and financial information for said dental patient;
   and wherein said dental presentation incorporates information from the dental desktop application into the dental presentation; and
   said clinical and financial information for said patient includes at least one of a name, an address, a picture, a chart and an insurance carrier.

29. The system of claim 28, wherein said dental desktop application comprises a dental practice management application.

* * * * *